US 6,693,167 B1

(12) United States Patent
Camilleri et al.

(10) Patent No.: US 6,693,167 B1
(45) Date of Patent: Feb. 17, 2004

(54) PEPTIDE-BASED GEMINI COMPOUNDS

(75) Inventors: Patrick Camilleri, Stevenage (GB); Andreas Kremer, Turnhout (BE); Simon Quentyn John Rice, Buntingford (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/581,068

(22) PCT Filed: Dec. 8, 1998

(86) PCT No.: PCT/GB98/03652

§ 371 (c)(1),
(2), (4) Date: Jun. 8, 2000

(87) PCT Pub. No.: WO99/29712

PCT Pub. Date: Jun. 17, 1999

(30) Foreign Application Priority Data

Dec. 9, 1997 (GB) ............................................. 9726073

(51) Int. Cl.[7] .................................................. C07K 7/02
(52) U.S. Cl. ........................ 530/328; 530/329; 530/330; 530/331; 514/15; 514/16; 514/17; 514/18; 514/19
(58) Field of Search ...................... 514/15–19; 530/330, 530/331, 328

(56) References Cited

FOREIGN PATENT DOCUMENTS

| DE | 196 22 612 | 10/1997 |
|----|------------|---------|
| EP | 0 394 111 | 6/1997 |
| WO | WO 95/19955 | 7/1995 |
| WO | WO 96/25388 | 8/1996 |
| WO | WO 97/11682 | 4/1997 |

OTHER PUBLICATIONS

N Tao et al.,Journal of Biological Chemistry, "CD36 is Palmitoylated on both N– and C–terminal Cytoplasmic Tails," Sep. 1996, vol. 271, No. 37, pp. 22315–22320.*

K Carpenter et al., Eur J Biochem., "Role of hydrophobic substituents in the interaction of opioid Ty dipeptide analogs with dodecylphosphocholine micelles," Nov. 1996, 1;241(3):756–64.*

Wadhwa, et al., "Peptide–Mediated Gene Delivery: Influence of Peptide Structure on Gene Expression", *Bioconjugate Chem.*, 8: 81–88 (1997).

Jennings, et al., "The Synthesis and Aggregation Properties of a Novel Anionic Gemini Surfactant", *Chem. Commun.*, No. 18: 1951–1952 (1998).

* cited by examiner

*Primary Examiner*—Christopher S. F. Low
*Assistant Examiner*—David Lukton
(74) *Attorney, Agent, or Firm*—William R. Majarian; Charles Kinzig; Stephen Venetianer

(57) ABSTRACT

New peptide-based Gemini compounds comprising two linked chains (a) each having: (1) a positively charged hydrophilic head, $Q^1$ or $Q^2$ formed from one or more amino acids and/or amines, (2) a central portion, P1 or P2, having a polypeptide backbone, and (3) a hydrophobic tail, $R^1$ or $R^2$, the central sections of each chain being linked together by bridge Y through residues in $P^1$ and $P^2$, are disclosed. Methods for their preparation and uses are also disclosed. Such uses include transfection of polynucleotides into cells in vivo.

22 Claims, 4 Drawing Sheets

PEPTIDE-BASED GEMINI COMPOUNDS

This invention relates to newly identified peptide-based gemini surfactant compounds, to the use of such compounds and to their production. The invention also relates to the use of the peptide-based gemini compounds to facilitate the transfer of compounds into cells for drug delivery.

Surfactants are substances that markedly affect the surface properties of a liquid, even at low concentrations. For example surfactants will significantly reduce surface tension when dissolved in water or aqueous solutions and will reduce interfacial tension between two liquids or a liquid and a solid. This property of surfactant molecules has been widely exploited in industry, particularly in the detergent and oil industries. In the 1970s a new class of surfactant molecule was reported, characterised by two hydrophobic chains with polar heads which are linked by a hydrophobic bridge (Deinega,Y et al., *Kolloidn. Zh.* 36, 649, 1974). These molecules, which have been termed "gemini" (Menger, FM and Littau,CA, *J.Am.Chem.Soc.* 113, 1451, 1991), have very desirable properties over their monomeric equivalents. For example they are highly effective in reducing interfacial tension between oil and water based liquids and have a very low critical micelle concentration.

Cationic surfactants have been used inter alia for the transfection of polynucleotides into cells in culture, and there are examples of such agents available commercially to scientists involved in genetic technologies (for example the reagent Tfx™-50 for the transfection of eukaryotic cells available from Promega Corp. WI, USA).

The efficient delivery of DNA to cells in vivo, either for gene therapy or for antisense therapy, has been a major goal for some years. Much attention has concentrated on the use of viruses as delivery vehicles, for example adenoviruses for epithelial cells in the respiratory tract with a view to corrective gene therapy for cystic fibrosis (CF). However, despite some evidence of successful gene transfer in CF patients, the adenovirus route remains problematic due to inflammatory side-effects and limited transient expression of the transferred gene. Several alternative methods for in vivo gene delivery have been investigated, including studies using cationic surfactants. Gao,X et al. (1995) *Gene Ther.* 2, 710–722 demonstrated the feasibility of this approach with a normal human gene for CF transmembrane conductance regulator (CFTR) into the respiratory epithelium of CF mice using amine carrying cationic lipids. This group followed up with a liposomal CF gene therapy trial which, although only partially successful, demonstrated the potential for this approach in humans (Caplen, N J. et al., *Nature Medicine*, 1, 39–46, 1995). More recently other groups have investigated the potential of other cationic lipids for gene delivery, for example cholesterol derivatives (Oudrhiri,N et al. *Proc.Natl.Acad.Sci.* 94, 1651–1656, 1997). This limited study demonstrated the ability of these cholesterol based compounds to facilitate the transfer of genes into epithelial cells both in vitro and in vivo, thereby lending support to the validity of this general approach.

These studies, and others, show that in this new field of research there is a continuing need to develop novel low-toxicity surfactant molecules to facilitate the effective transfer of polynucleotides into cells both in vitro for transfection in cell-based experimentation and in vivo for gene therapy and antisense treatments. The present invention seeks to overcome the difficulties exhibited by existing compounds.

The invention relates to the peptide-based gemini compounds comprising two linked chains:

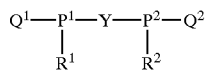

each chain having:
(1) a positively charged hydrophilic head, $Q^1$ or $Q^2$, formed from one or more amino acids and/or amines;
(2) a central portion, $P^1$ or $P^2$, having a polypeptide backbone; and
(3) a hydrophobic tail, $R^1$ or $R^2$; the central sections of each chain being linked together by bridge Y through residues in $P^1$ and $P^2$.

Preferably the central portion is made up of two or three amino acids, $P^a$ (optional), $P^b$ and $P^c$, in which:
$P^a$ is a D- or L- amino acid, preferably hydrophilic, such as threonine or serine,
$P^b$ is preferably D- or L- cysteine, serine or threonine, and
$P^c$ is preferably D- or L- serine or threonine and is linked to $R^1$ or $R^2$.

Preferred compounds of the present invention include compounds of the formula (I):

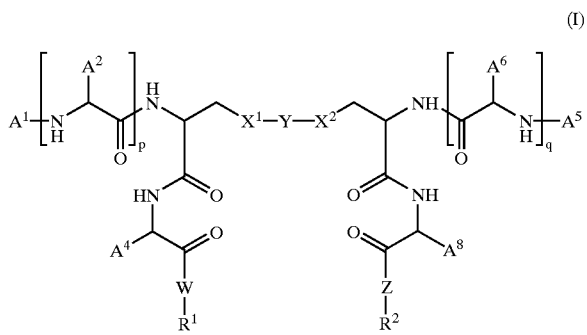

where:
$A^1$ and $A^5$ which may be the same or different, is a positively charged group formed from one or more amino acids or amines joined together in a linear or branched manner and preferably bonded by an amide (CONH) bond;
$A^2/A^6$CH(NH)CO, which may be the same or different, is derived from an amino acid, preferably serine;
p and q, which may be the same or different, is 0 or 1;
$X^1/X^2$CH$_2$CH(NH)CO, which may be the same or different, is derived from cysteine ($X^1/X^2$=S), serine or threonine ($X^1/X^2$=O);
$A^4/A^8$CH(NH)CO, which may be the same or different, is derived from serine or threonine;
Y is a linker group, preferably (CH$_2$)$_m$ where m is an integer from 1 to 6, most preferably 2, and may be a disulphide bond when $X^1$ and $X^2$ is each S;
$R^1$ and $R^2$ are C$_{(10-20)}$ saturated or unsaturated alkyl groups, and
W and Z are NH, O, CH$_2$ or S; or
a salt, preferably a pharmaceutically acceptable salt thereof.

Preferably, the compound is symmmetrical, that is $A^1$ and $A^5$ are the same, $A^2$ and $A^6$ are the same, $A^4$ and $A^8$ are the same, $R^1$ and $R^2$ are the same, and W and Z are the same.

Representative examples of $A^1/A^5$ include D- or L-amino acids selected from arginine, lysine, ornithine and histidine, preferably lysine, or amines such as spermine and spermidine. Up to seven amino acids and/or amines may be linked in a linear or branched chain. Prefered examples include groups having two or three lysines or ornithines or a combination of lysine, ornithine, arginine and histidine, for instance:

or

COCH(NHR)(CH$_2$)$_3$NHCO(NH$_2$)(CH$_2$)$_3$NH$_2$ or

COCH(NHR)(CH$_2$)$_4$NHCO(NH$_2$)(CH$_2$)$_3$NH$_2$ in which R is H or NHCO(NH$_2$)(CH$_2$)$_4$NH$_2$ or NHCO(NH$_2$)(CH$_2$)$_3$NH$_2$ Preferably, —X$^1$—Y—X$^2$— is —SCH$_2$CH$_2$S— or —OCH$_2$CH$_2$O—

Preferably, R$^1$ and R$^2$ is each a C$_{12}$–C$_{20}$ alkyl group, for instance C$_{12}$.

Preferably, W and Z is NH, thereby forming a further amide (CONH) bond.

Compounds of the present invention may be prepared from readily available starting materials using synthetic peptide chemistry well known to the skilled person. For prefered compounds of the present invention a useful intermediate is the compound:

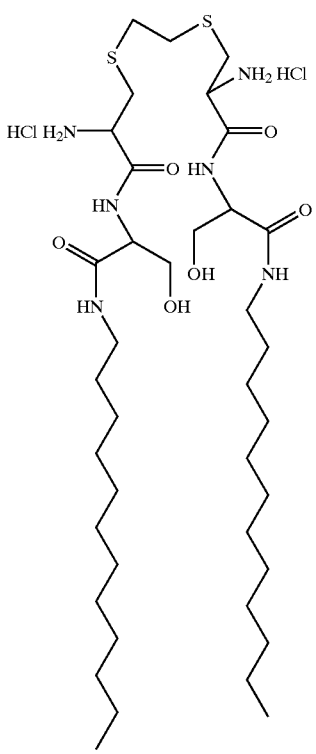

39 which is synthesised in a multi-stage process beginning, for instance, with the construction of the di-cysteine part and subsequently building up the hydrophilic head by attaching a serine moiety at the carboxyl group of each cysteine moiety, using standard peptide chemistry, and then attaching the hydrocarbon chains to the carboxyl group of the serine moiety using a standard amide forming reaction well known to those skilled in the art. This intermediate can then be taken through to compounds of formula (I) by further reaction at the nitrogens of the cysteine residues.

Another aspect of the invention relates to methods for using the peptide-based gemini compounds. Such uses include facilitating the transfer of oligonucleotides and polynucleotides into cells for antisense, gene therapy and genetic immunisation (for the generation of antibodies) in whole organisms. Other uses include employing the compounds of the invention to facilitate the transfection of polynucleotides into cells in culture when such transfer is required, in, for example, gene expression studies and antisense control experiments among others. The polynucleotides can be mixed with the compounds, added to the cells and incubated to allow polynucleotide uptake. After further incubation the cells can be assayed for the phenotypic trait afforded by the transfected DNA, or the levels of mRNA expressed from said DNA can be determined by Northern blotting or by using PCR-based quantitation methods for example the Taqman® method (Perkin Elmer, Connecticut, USA). Compounds of the invention offer a significant improvement, typically between 3 and 6 fold, in the efficiency of cellular uptake of DNA in cells in culture, compared with compounds in the previous art. In the transfection protocol, the gemini compound may be used in combination with one or more supplements to increase the efficiency of transfection. Such supplements may be selected from, for example:

(i) a neutral carrier, for example dioleyl phosphatidylethanolamine (DOPE) (Farhood, H., et al (1985) *Biochim. Biophys. Acta* 1235 289);

(ii) a complexing reagent, for example the commercially available PLUS reagent (Life Technologies Inc. Maryland, USA) or peptides, such as polylysine or polyornithine peptides or peptides comprising primarily, but not exclusively, basic amino acids such as lysine, ornithine and/or arginine. The list above is not intended to be exhaustive and other supplements that increase the efficiency of transfection are taken to fall within the scope of the invention.

In still another aspect, the invention relates to the transfer of genetic material in gene therapy using the compounds of the invention.

Yet another aspect of the invention relates to methods to effect the delivery of non-nucleotide based drug compounds into cells in vitro and in vivo using the compounds of the invention.

The following definitions are provided to facilitate understanding of certain terms used frequently herein.

"Amino acid" refers to dipolar ions (zwitterions) of the form $^+$H$_3$NCH(R)CO$_2^-$. They are differentiated by the nature of the group R, and when R is different from hydrogen can also be asymmetric, forming D and L families. There are 20 naturally occurring amino acids where the R group can be, for example, non-polar (e.g. alanine, leucine, phenylalanine) or polar (e.g. glutamic acid, histidine, arginine and lysine). In the case of un-natural amino acids R can be any other group which is not found in the amino acids found in nature.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Transfection" refers to the introduction of polynucleotides into cells in culture using methods involving the modification of the cell membrane either by chemical or physical means. Such methods are described in, for example, Sambrook et al., *MOLECULAR CLONING: A LABORATORY MANUAL*, 2nd Ed., Cold Spring Harbor Laboratory Press, Cold Spring Harbor, N.Y. (1989). The polynucleotides may be linear or circular, single-stranded or double-stranded and may include elements controlling replication of the polynucleotide or expression of homologous or heterologous genes which may comprise part of the polynucleotide.

The invention will now be described by way of the following descriptions and examples.

DESCRIPTIONS

Description 1

Bisthioether 3

A 1L 3-necked flask equipped with mechanical stirrer, reflux condenser and dropping funnel was flushed with $N_2$ directly into the flask through the condenser. A solution of 31.3 g (0.20 mole) L-cysteine.hydrochloride.$xH_2O$ (1) in 100 ml (degassed ultrasonic for 10 minutes) was added to the flask. A degassed solution of 34 g (0.40 mole) $NaHCO_3$ in 300 ml $H_2O$ was added, followed by the dropwise addition (30 minutes) of a degassed solution of 18.8 g (8.6 ml; 0.10 mole) 1,2-dibromoethane (2) in 100 ml EtOH. After another 30 minutes the mixture was heated to 65–70° C. and stirred, still under $N_2$, for another 3 hours (within 1 minutes precipitation started). The mixture was cooled to 20° C., filtered, rinsed with 30 ml $H_2O$ and with 100 ml acetone (2x). After drying 19.4 g white solid was obtained which still contained some free cysteine ($^1$H NMR). The solid was suspended in 250 ml 2.5% $NH_4OH$ and 25% $NH_4OH$ was added until a clear solution was obtained. To this solution 15 mg KCN was added and the mixture was stirred for 30 minutes. The solution was acidified to pH6 using HOAc and stirred for 30 minutes whilst cooling to 5° C. The solid was collected, rinsed with $H_2O$ (100 ml), acetone (2×100 ml) and dried, yielding 18.1 g (68%) 3 as a white solid.

Description 2

Boc-L-Leucine 5

19.7 g (0.15 mole) L-Leucine 4 was suspended in 200 ml$H_2O$ and 6.75 g (0.17 mole) NaOH was added. The clear solution was cooled to <10° C. and a solution of 36 g (0.165 mole) $(BOC)_2O$ in 100 ml THF was added dropwise keeping T<10° C. (30 minutes). After stirring for 4 hours at room temperature the mixture was acidified to pH2 by adding 1N HCl. The mixture was extracted with EtOAc (250, 100 and 100 ml), the combined organic layers were dried on $Na_2SO_4$ and evaporated, yielding 40 g (>100%) 5 as a colorless oil which contained some THF but was used as such.

Description 3

Boc-L-Leucine-OSuc 7

40 g crude 5 (max. 0.15 mole) was dissolved in 400 ml THF (distilled prior to use from LAH) under $N_2$. After addition of 17.3 g (0.15 mole) N-hydroxysuccinimide (6) and 30.9 g (0.15 mole) DCC the mixture was stirred for 3.5 hours at room temperature. The mixture was filtered over a $P_2$ glassfilter, the filter was rinsed with 50 ml THF and the filtrate was evaporated. The residue was dissolved in 400 ml refluxing isopropylether, the solution was filtered hot and the filtrate was placed at 4° C. for 20 hours. The solid was collected, rinsed with 50 ml IPE and dried, yielding 32 g (65%) 7 as a white solid.

Description 4

Compound 8

8.05 g (30mmole) 3 was suspended in 200 ml $H_2O$ and after addition of 8.3 g (60 mmole) $K_2CO_3$ the mixture was heated to get a clear solution. After cooling to room temperature a solution of 19.7 g (60mmole) 7 in 200 ml THF was added at once. The mixture was stirred at room temperature for 20 hours, followed by acidification to pH 6 (30% HCl). After filtration the filtrate was acidified to pH2–3 (30% HCl) and extracted with $CHCl_3$ (250, 100 and 100 ml). The combined organic layers were once washed with brine (50 ml), dried on $Na_2SO_4$ and evaporated, yielding 23 g crude 8 as a white foam which was used as such.

Description 5

Compound 9

23 g crude 8 was dissolved in 200 ml EtOAc, cooled to 0° C. and HCl-gas was bubbled through for 1 hour, followed by stirring at this temperature for another hour. The solid was collected, rinsed with ether and dried under vacuo over KOH. This yielded 15.4 g (91%) 2 as a hygroscopic nearly white solid.

Description 6

Compound 10

17.0 g (30 mmole) 2 dissolved in 250 ml $H_2O$ and after cooling to <10° C. in an ice/waterbath 7.2 g (180 mmole) NaOH was added. After stirring for 10 minutes at room temperature a solution of 14.4 g (66 mmole) lauroylchloride in 50 ml THF was added dropwise in 5 minutes. The mixture was stirred for 20 hours and extracted with hexame (2×150 ml). A 3-layer system formed and the lower 2 layers were acidified to pH 1–2 (1 N HCl) and extracted with ether (200, 100, 100 and 50 ml). The combined ether layers were dried on MgSO4 and evaporated, yielding 24 g (93%) 10 as an oil/foam. This material was used as such.

Description 7

Compound 11

24 g (max 27.5 mmole) 10 dissolved in 400 ml THF (distilled from LAH) under $N_2$. After addition of 6.33 g (55 mmole) N-hydroxysuccinimide (6) and 11.33 g (55 mmole) DCC the mixture was stirred at room temperature for 20 hours. The mixture was filtered over a large $P_2$ glassfilter, another 250 ml THF was added to speed up filtration. The filter was rinsed with another 100 ml THF. The filtrate was evaporated yielding 40 g white solid and this crude material was recristallized from 400 ml IPA. Stirred 1 hour 0° C. and collected. After drying 22.3 g (77%) 11 was obtained as white solid.

Description 8

Compound 13

542 mg (2.2 mmole) H.Arg.$NH_2$.2HCl (12) was dissolved in 15 ml $H_2O$ and 304 mg (2.2 mmole) $K_2CO_3$ was added. A solution of 1.05 g (1.0 mmole) 11 in 15 ml THF was added at once and the mixture was stirred at room temperature for 20 hours. Most of the THF was evaporated and an oil formed in the waterlayer. This suspension was extracted with ether (6×50 ml), the combined ether layers were dried on $MgSO_4$ and evaporated, yielding 9500 mg (82%) 13 free amine as a yellow solid. Treatment of this material with HCl-gas in EtOAc/$CH_2Cl_2$ gave 13 as a yellow solid.

Description 9

Compound 15

5.25 g (5.0 mmole) 11 dissolved in 50 ml THF (some heating was needed) and a solution of 1.31 g (10.5 mmole) Taurine (14) and 1.45 g (10.5 mmole) $K_2CO_3$ in 50 ml $H_2O$ was added at once. After stirring at room temperature for 20 hours most of the THF was removed by evaporation and 300 ml MeOH was added. Mixture placed at −20° C. for 20 hours, solid collected, rinsed with MeOH and dried. This yielded 3.3 g 15 contaminated with N-hydroxysuccinimide, which was combined with 700 mg impure material of an other run. This 4.0 g was recrystallized from 200 ml MeOH+ 50ml $H_2O$. Some solid was removed by filtration and the clear filtrate was placed at −20° C. for 2 hours, the solid was colected, rinsed with MeOH and dried. This yielded 2.0 g 15 as an off white solid. A $2^{nd}$ crop of 800 mg was obtained from the filtrate.

Description 10

Compound 16

1.05 g (1.0 mmole) 11 was dissolved in 20 ml THF and a solution of 275 mg (2.2 mmole) 2-aminoethylphosphonic acid and 300 mg (2.2 mmole) $K_2CO_3$ in 20 ml $H_2O$ was added at once. After stirring at room temperature for 20 hours most of the THF was removed by evaporation and the aqueous solution was freeze dried. This yielded a white solit which was recrystallized from 20 ml MeOH and placed at −20° C. for 20 hours. The solid was collected and dried yielding 150 mg. $^1H$ NMR showed it to be N-hydroxysuccinimide. The filtrate was evaporated and the remaining yellow oil was dissolved in 10 ml refluxing MeOH and after addition of 20 ml IPA placed at −20° C. for 4 hours. Solid was collected and dried, yielding 260 mg.

The filtrate was evaporated, dissolved in 20 ml EtOAc and placed at −20° C. for 20 hours. The solid was collected.

Description 11

Compound 17

1.05 g (1.0 mmole) 11 was dissolved in 20 ml THF and a solution of 310 mg (2.2 mmole) O-phosphocolamine and 300 mg (2.2 mmole) $K_2CO_2$ in 20 ml $H_2O$ was added at once. After stirring at room temperature for 20 hours most of the THF was removed by evaporation and the aqueous solution was freeze dried. The white solid was recrystallized from 20 ml MeOH and placed at −20° C. for 20 hours. The solid was collected, rinsed with MeOH and dried. This yielded 310 mg white solid. No product. The filtrate was evaporated and the remaining yellow solid was dissolved in 10 ml MeOH, 20 ml IPA was added and the mixture was placed at −20° C. for 20 hours. Solid collected, 20–30 mg Filtrate evaporated, residue dissolved in 25 ml EtOAc, placed at −20° C. and after 20 hours the solid was collected.

Description 12

Boc-Glycine Boc-Glycine 19

18.8 g (0.25 mole) Glycine 18 was suspended in 250 ml $H_2O$ and 11 g (0.275 mole) NaOH was added. The clear solution was cooled to <10° C. and a solution of 60 g (0.165 mole) $(BOC)_2O$ in 250 ml THF was added dropwise keeping T<10° C. (20 minutes). After stirring for 20 hours at room temperature the mixture was acidified to pH1 by adding 1N HCl. The mixture was extracted with EtOAc (250, 100 and 100 ml), the combined organic layers were dried on $MgSO_4$ and evaporated, yielding 47.5 g (>100%) 5 as a colourless oil which contained some THF but was used as such.

Description 13

Boc-Glycine-OSuc 20

47.5 g crude 19 (max. 0.25 mole) was dissolved in 500 ml THF (distilled prior to use from LAH) under $N_2$. After addition of 30 g (0.26 mole) N-hydroxysuccinimide (6) and 53.5 g (0.26 mole) DCC at <10° C., the mixture was stirred for 20 hours at room temperature. Now the mixture was filtered over 1 cm celite on a P2 glassfilter, the filter was rinsed with 200 ml THF and the filtrate was evaporated. The crude material (56 g) was recrystallized from refluxing isopropylether/THF (600 ml 1:1), the solution was filtered hot and the filtrate was stirred at 0C for 3 hours. The solid was collected, rinsed with 50 ml IPE and dried, yielding 16.4 g (24%) 20 as a white solid. Filtrate evaporated and stored.

Description 14

Compound 21

8.05 g (30 mmole) 3 was suspended in 200 ml $H_2O$ and after addition of 8.3 g (60 mmole) $K_2CO_3$ the mixture was heated to get a clear solution. After cooling to <40° C. a solution of 16.3 g (60 mmole) 20 in 200 ml THF was added in 4 portions within 2 minutes. The mixture was stirred at room temperature for 72 hours, followed by acidification to pH 6 (30% HCl). After filtration the filtrate was acidified to pH 2–3 (30% HCl) and extracted with $CHCl_3$ (250, 100 and 100 ml). The combined organic layers were once washed with brine (50 ml), dried on $MgSO_4$ and evaporated, yielding 15.8 g (90%) 21 as a white foam which was used as such.

Description 15

Compound 22

15.8 g (27 mmole) crude 21 was dissolved in 300 ml EtOAc and HCl-gas was bubbled through for 1 hour, followed by stirring at 0° C. in an ice/waterbath and a solution of 12.2 g (56 mmole) lauroylchloride in 50 ml THF was added at once. The mixture was stirred for 20 hours and extracted with hexane (2×100 ml). The water layer was acidified to pH 1–2 (1 N HCl) and extracted with ether (3×150 ml). A solid formed during extraction, which was collected and dried. This yielded 7.5 g (39%) 23 white solid.

The filtrate was evaporated and the remaining slurry was stirred in 250 ml $Et_2O$. An attempt to collect the solid failed and addition of 25 ml MeOH gave a clear solution. This solution was placed at −20° C. for 20 hours. The solid was collected, rinsed with ether and dried.

Description 16

Compound 24

7.47 g (10 mmole) 23 dissolved in 200 ml THF (distilled from LAH) under $N_2$. After addition of 2.53 g (22 mmole) N-hydroxysuccinimide (6) and 4.53 g (22 mmole) DCC the mixture was stirred at room temperature for 72 hours. The mixture was filtered over a 1 cm layer celite on a large $P_2$ glassfilter (very slow). The filtrate was evaporated yielding 1.90 g 24 as a foam.

The filer was rinsed with 300 ml dioxane and the filtrate was evaporated yielding 6.9 g 24 as a foam. Total yield 8.8 g (94%).

Description 17

Compound 25

542 mg (2.2 mmole) H.Arg.$NH_2$.2HCl (12) was dissolved in 15 ml $H_2O$ and 750 mg (5.4 mmole) $K_2CO_3$ was added.

A solution of 941 mg (1.0 mmole) 24 in 15 ml THF was added at once and the mixtrue was stirred at room temperature for 20 hours. Most of the THF was evaporated and the waterlayer was extracted with EtOAc (2×50 ml), the combined EtOAc layers were dried on $MgSO_4$ and evaporated, yielding 150 mg 25 free amine as a foam. Both portions were combined and dissolved in $CH_2Cl_2$ and after the addition of 75 ml EtOAc, HCl-gas was bubbled through for 1.5 hour. Now the mixture was cooled to 0° C. and stirred for another 2 hours. Attempts to collect the solid failed, so 100 ml ether was added and the mixture was stirred at room temperature for 20 hours. The solid was collected, rinsed with ehter and dried, yielding 520 mg 25 as a slightly brown solid.

Description 18
Compound 26

250 mg (2.0 mmole) taurine (14) was dissolved in 15 ml $H_2O$ and 280 mg (2.0 mmole) $K_2CO_3$ was added. Now a solution of 941 mg (1.0 mmole) 24 in 15 ml THF was added at once and the mixture was stirred at room temperature for 20 hours. Most of the THF was evaporated and the aqueous solution was freeze dried. The resulting white solid was recrystallized from 30 ml MeOH, stirred 3 hours at 0° C. and the solid was collected, rinsed with ether and dried.

This yielded 225 mg 26 as a white solid.

The filtrate was partly evaporated and placed at –20° C. for 20 hours. The solid was collected, rinsed with ether and dried, yieleing 210 mg 26 as a white solid. Both portions were combined.

Description 19
Compound 27

26.8 g (0.1 mole) 3 was suspended in 300 ml $H_2O$ and 9.6 g (0.24 mole) NaOH was added. A clear solution formed within 5 minutes, the mixture was cooled to <10° C. and a solution of 43.6 g (0.2 mole) $BOC_2O$ in 300 ml THF was added dropwise in 30 minutes. The mixture was stirred at room temperature overnight. After addition of a solution of 2.5 g (0.06 mole) NaOH in 25 ml $H_2O$ and 15 g (0.07 mole) $BOC_2O$ in 75 ml THF the mixture was stirred for another 18 hours.

The mixtue was acidified to pH 2 by adding 2N HCl and after addition of 300 ml brine, extracted with THF (3×400 ml) and EtOAc (2×300 ml) The combined organic layers were dried on $MgSO_4$ and evaporated, yielding 42 g white solid. This solid was recrystallized from MEK/pentane, stirred at room temperature for 2 hours and placed at –20° C. for 2 hours. The solid was collected and dried, yielding 37.8 g (81%) 27 as a white solid.

Description 20
Compound 28

8.9 g (19 mmole) 27 was dissolved in 300 ml THF (from LAH) under $N_2$ and 4.37 g (38 mmole) 6 and 7.38 g (38 mmole) DCC were added. After stirring at room temperature for 18 hours the mixture was filtered over 1 cm celite, the filter was rinsed with another 300 ml THF and the filtrate was evaporated yielding 11.1 g (88%) 28 as a white solid.

Description 21
Compound 29

2.7 g (20.6 mmole) L-leusine (4) and 2.8 g (20.3 mmole) $K_2CO_2$ were dissolved in 100 ml $H_2O$ and a suspension of 6.6 g (10 mmole) 28 in 50 ml dioxane was added. The mixture was stirred at room temperature for 20 hours and most of the dioane was removed by evaporation. The aqueous solution was extracted with 50 ml ether and acidified to pH 1 by addition of 30% HCl. Now the mixture was extracted with $CHCl_3$ (150, 100 and 50 ml), the combined organic layers were washed with brine (200 ml), dried on $MsSO_4$ and evaporated, yielding a white foam which was stripped with THF to get 7.5 g (>100%) 29 as a solid white foam.

Description 22
Compound 30

7.5 g crude 29 (max. 10 mmole) was dissolved in 100 ml THF (from LAH) under $N_2$, 2.3 g (20 mmole) N-hydroxysuccinimide (6) and 4.12 g (20 mmole) DCC were added and the mixture was stirred at room temperature for 20 hours. The mixture was filtered over 1 cm celite, the filter was rinsed with THF and the filtrate was evaporated, yielding 9.5 g white foam which was recrystallized from 75 ml IPA and placed at –20° C. for 3 hours. The solid was collected but liquified immediately on the glass filter. The oily material was dissolved in 20 ml THF and evaporated, yielding 6.5 g (73%) 30 as a solid white foam.

Description 23
Compound 31

6.5 g (7.3 mmole) 30 was dissolved in 100 ml THF and after addition of 2.78 g (15 mmole) dodecylamine the mixture was stirred at room temperature for 18 hours. After evaporation a foam was obtained which was dissolved in 100 ml $CHCl_3$. The solution was washed with $H_2O$ (2×75 ml), dried on $MgSO_4$ and evaporated, yielding 7.5 g (100%) 31 as a solid foam.

Description 24
Compound 32

7.5 g (7.3 mmole) crude 31 was dissolved in 250 ml EtOAc under heating and after cooling to room temperature HCl-gas was bubbled through for 2 hours. Stirring was continued at 0° C. for 3 hours. The solid was collected, rinsed with ether and dried under vacuo over KOH. This yielded 4.0 g (60%) 32 as a white solid.

Description 25
Compound 33

903 mg (1.0 mmole) 32 was dissolved in 10 ml $H_2O$ under heating (gel formed), after cooling to room temperature, 80 mg (2.0 mmole) NaOH dissolved in 2 ml $H_2O$ was added. A suspension was formed and THF was added until a clear solution was obtained. Now a solution of 572 mg (2 mmole) BOC-B-alaOSuc (2) in 5 ml THF was added and the mixture was stirred at room temperature for 5 hours. Most of the THF was removed by evaporation, another 30 ml $H_2O$ was added and after stirring for another hour the solid was collected, rinsed with 10 ml $H_2O$ and dried. This yielded 1.0 g (85%) 33 as an off white solid.

Description 26
Compound 34

1.0 g (0.85 mmole) 33 suspended in 25 ml EtOAc and 25 ml $CH_2Cl_2$ added to get a clear solution. HCl-gas bubbled through for 1.5 hour and stirred at 0° C. for another 2 hours. No solid had formed so most of the $CH_2Cl_2$ was removed by evaporation and stirring at 0° C. was continued for another 30 minutes. The solid was collected, partly by filtration (very slow), mainly be centrifugation. Total yield after drying 810 mg (91%) 34 as a yellow solid.

Description 27
Compound 36

4.2 g (40 mmole) L-serine 35 and 5.53 (40 mmole) $K_2CO_3$ were disslved n 300 ml $H_2O$ and a suspension of 12.8 g (max. 19 mmole) 28 in 300 ml THF was added. The mixture was stirred at room temperature for 72 hours and most of the THF was removed by evaporation. The aqueous solution was acidified to pH 1 by addition of 1N HCl. The mixture was extracted with $CH_2Cl_2$+15% MeOH (250, 100 and 100 ml), the combined organic layers were dried on $MgSO_4$ and evaporated, yielding 8.5 g (70%) 36 as a white solid foam which was used as such.

Description 28

Compound 37

8.5 g (max. 13.2 mmole) 36 was dissolved in 200 ml THF (from LAH) under $N_2$ and after addition of 3.46 g (30 mmole) N-hydroxysuccinimide (6) and 6.2 g (30 mmole) DCC the mixture was stirred at room temperature for 24 hours. The mixture was filtered over 1cm celite, the filter was rinsed with 50 ml THF and evaporated. This yielded 12.5 g (>100%) 37 as a white foam which was used as such.

Description 29

Compound 38

12.5 g crude (max 13.2 mmole) 37 was dissolved in 200 ml THF and stirred with 5.0 g (27 mmole) dodecylamine at room temperature for 48 hours. The THF was removed by evaporation and the residue was dissolved in 250ml $CHCl_3$ and extracted with brine (2×150 ml). The combined brine layers were extracted with 50 ml $CHCl_3$ and the combined $CHCl_3$ layers were dried on $MgSO_4$ and evaporated. This yielded 15.4 g (>100%) 38 as a nearly white solid which was used as such.

EXAMPLES

Example 1

Compound 39

2-Amino-3-{2-[2-amino-2-(1-dodecylcarbamoyl-2-hydroxy-ethylcarbamoyl)-ethylsulphanyl]-ethylsulphonyl}-N-(1-dodecylcarbamoyl-2-hydroxy-ethyl-)-propionamide 15.4 g (max. 13.2 mmole) 38 dissolved in 400 ml EtOAc and HCl-gas was bubbled through for 1.5 hour. The mixture was stirred at 0° C. for 2 hours, the solid was collected, rinsed with ether and dried, yielding 9.9 g (88%) 39 as a white solid.

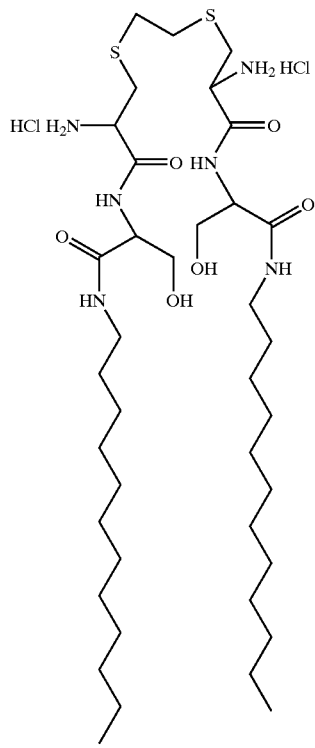

Example 2

Compound 40

4.25 g (5 mmole) 39 was dissolved in 100 ml $H_2O$ with heating and after cooling to <40° C. a solution of 460 mg (10 mmole) NaOH in 10 ml $H_2O$ was added. A suspension formed and THF was added until a clear solution was obtained (150 ml). Next 2.86 g (10 mmole) BOC-β-alaOSu (42) was added and the mixture was stirred at room temperature for 20 hours. Most of THF was removed by evaporation, another 100 ml $H_2O$ was added and the mixture was stirred at 0° C. for 3 hours; The solid was collected, rinsed with 20 ml $H_2O$ and dried. This yielded 5.2 g (93%) 40 as a nearly white solid.

Example 3

Compound 41

5.2 g (4.6 mmole) 40 was dissolved in 100 ml $CH_2Cl_2$ and 200 ml EtOAc was added. HCl-gas was bubbled through for 1.5 hour and stirring was continued at 0° C. for 2 hours. The solid was collected, rinsed with ether and dried, yielding 4.7 g (100%) 41 as off white solid.

Example 4

Compounds 42 and 43

After neutralization of compounds 34 and 41 using 2 eq. of NaOH in MeOH both compounds were treated with $(CH_2O)_n$ and $NaCNBH_3$ under $N_2$ for 18 hours. In both reactions complex mixtures were formed, probably due to alkylation on amide nitrogen as well.

Example 5
Compound 44

332 mg (0.39 mmole) 39 was dissolved in 15 ml $H_2O$ under heating and after cooling to <40° C. a solution of 33 mg (0.83 mmole) NaOH in 1 ml $H_2O$ was added. A white suspension formed and THF was added until a clear solution was obtained (25 ml). To this solution 499 mg (0.78 mmole) BOC-Arg(Z)$_2$-OSu (47) was added and the mixture was stirred at room temperature for 20 hours. Most of the THF was evaporated and another 15 ml $H_2O$ was added. After 2 hours stirring the solid was collected, rinsed with $H_2O$ and dried, yielding 700 mg (98%) 44 as a white solid.

Example 6
Compound 45

100 mg (0.05 mmole) 44 was dissolved in 20 ml HOAc and 500 mg 10% Pd on Carbon (0.5 mmole Pd) was added. The mixture was stirred under $H_2$ (5 bar) for 48 hours. The mixture was filtered over 1 cm celite, the filter was rinsed with 10 ml HOAc and the filtrate was evaporated. This yielded 100 mg crude 45 as a green oil.

Example 7
Compound 46

100 mg crude 45 (max 0.05 mmole) was disslved in 10 ml $CH_2Cl_2$ and 10 ml EtOAc was added. HCl-gas was bubbled through for 1 hour and the mixture was stirred 18 hours at room temperature. Most of the $CH_2Cl_2$ was removed by evaporation, 30 ml ether was added and the mixture was stirred at 0° C. for 1 hour. No crystalline material had formed so the mixture was evaporated, yielding 75 mg crude 46 as a yellow oil.

Example 8
Compound 49

850 mg (1.0 mmole) 39 was dissolved in 20 ml $H_2O$ and after 88 mg (2.2 mmole) NaOH was added a suspension formed. Now THF was added until a clear solution was obtained (30 ml) and 974 mg (2.2 mmole) BOC$_2$LysOSuc (compound 48) was added. After stirring at room temperature for 20 hours most of the THF was removed by evaporation, another 20 ml $H_2O$ was added and the mixtrue was stirred for 2 hours. The solid was collected, rinsed with $H_2O$ and dried, yielding 1.35 g (90%) 49 as a white solid.

Example 9
Compound 50

500 mg 49 was dissolved in 25 ml $CH_2Cl_2$ and after addition of 25 ml EtOAc HCl-gas was bubbled through for 1 hour, the mixture was stirred at 0° C. for 1.5 hour. An attempt to collect the solid failed, 40 ml ether was added and stirring was continued for 18 hours. The solid was collected, rinsed with ehter and dried, yielding 290 mg 50 as a white solid.

Example 10
Compound 51

425 mg (0.43 mmole) 41 was dissolved in 20 ml $H_2O$ and 44 mg (1.1 mmole) NaOH was added. A suspension formed and THF was added until a clear solution was obtained (25 ml). After addition of 487 mg (1.1 mmole) 48 the mixture was stirred at room temperature for 20 hours. Most of the THF was evaporated, another 20 ml $H_2O$ was added and after stirring for 1.5 hour the solid was collected, rinsed with $H_2O$ and dried. This yielded 750 mg 51 as a white solid.

Example 11
Compound 52

250 mg 51 was dissolved in 30 ml $CH_2Cl_2$ and after addition of 30 ml EtOAc, HCl-gas was bubbled through for 1 hour, the mixture was stirred at 0° C. for 1.5 hour. The solid was collected, rinsed with ether and dried, yielding 120 mg 52 as a white salt.

Example 12
Compound 57 (SucOSerLysBOC$_2$)

4.43 g (10 mmole) BOC$_2$LysOSuc (48) was dissolved in 5 ml THF and a solution of 1.16 g (11 mmole) L-serine and 1.52 g (11 mmole) $K_2CO_3$ in 50 ml $H_2O$ was added immediately. The mixture was stirred at room temperature for 72 hours. Most of the THF was removed by evaporation and the remaining slurry was acidified to pH2 by the addition of 1M HCl and extracted with $CHCl_2$ (2×75 ml). The combined organic layers were dried (Na$_2$SO$_4$) and evaporated, yielding 57 as a white solid foam which was used as such in example 43.

Example 13
Compound 54

850 mg (1.0 mmole) 39 was dissolved in 30 ml $H_2O$ and 88 mg (2.2 mmole) NaOH was added, followed by the addition of 30 ml THF to get a clear solution. A solution of 1.5 g (max. 2.3 mmole) 57 in 30 ml THF was added immediately and the solution was stirred at room temperature for 48 hours. Most of the THF was removed by evaporation, another 30 ml $H_2O$ was added and stirring was continued for 1 hour. Because no solid had formed, the mixture was extracted twice with 75 ml EtOAc/ether (2:1). The combined organic layers were dried (Na$_2$SO$_4$) and evaporated yielding the BOC-protected intermediate as a solid foam.

This foam was dissolved in 25 ml $CH_2Cl_2$ and 50 ml EtOAc was added. HCl gas was bubbled through the clear solution for 1 hour and stirring was continued at 0° C. for another hour. The salt was collected, rinsed with ether and dried under vacuum, yielding 1.15 g (85%) 54 as a slightly brown solid.

Example 14
Compound 55

1.18 g (1.0 mmole) 50 was dissolved in 25 ml $H_2O$ and 176 mg (4.4 mmole) NaOH was added, followed by the addition of 30 ml THF to get a clear solution. 974 mg (2.2 mmole) 48 were added and the mixture stirred at room temperature for 48 hours. Most of the THF was removed by evaporation, another 50 ml $H_2O$ was added and the mixture was stirred for 2 hours. Because no solid was formed the mixture was extracted with ether (2×100 ml), the combined organic layers were dried (Na$_2$SO$_4$) and evaporated, yielding 2 g of the BOC-protected intermediate as a solid foam. The foam was dissolved in 50 ml EtOAc and HCl-gas was bubbled through the solution for 1 hour and stirring was continued at 0° C. for another hour. The salt was collected, rinsed with ether and dried under vacuum, yielding 1.15 g (76%) 55 as a nearly white solid.

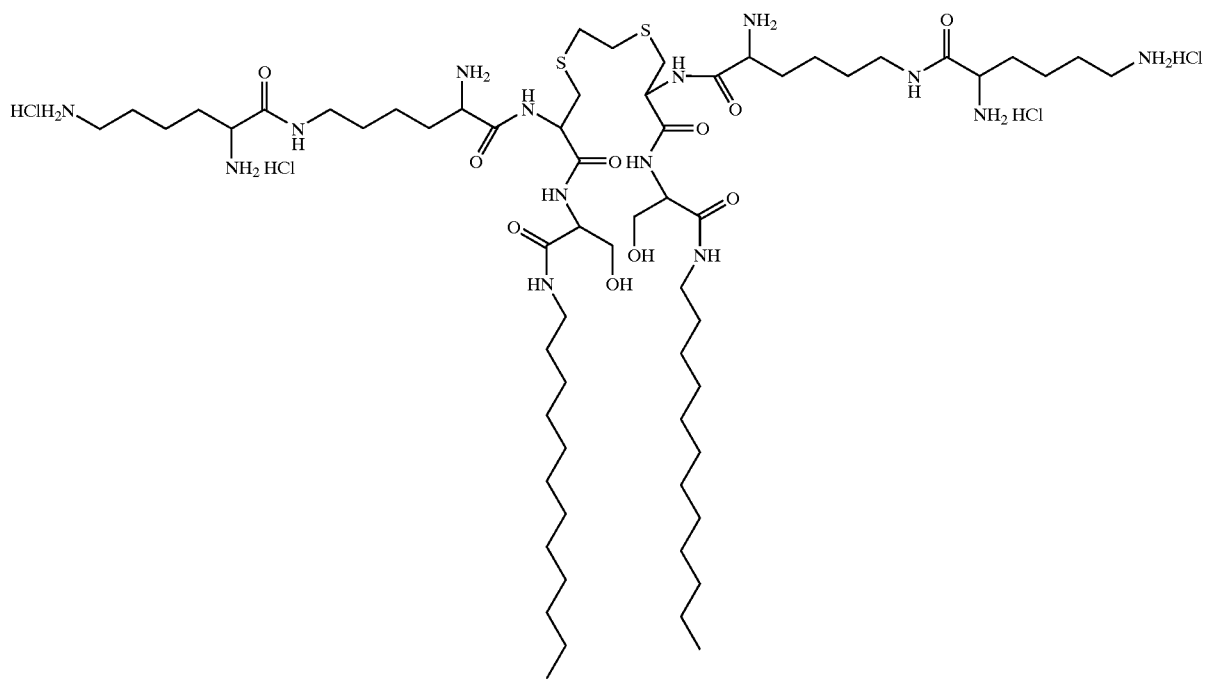
Example 15
Compound 56
Compound 56 was synthesised as for compound 55 except that 1.95 g (4.4 mmole) 48 was used. This yielded 1.1 g (60%) 56 as an off white solid.
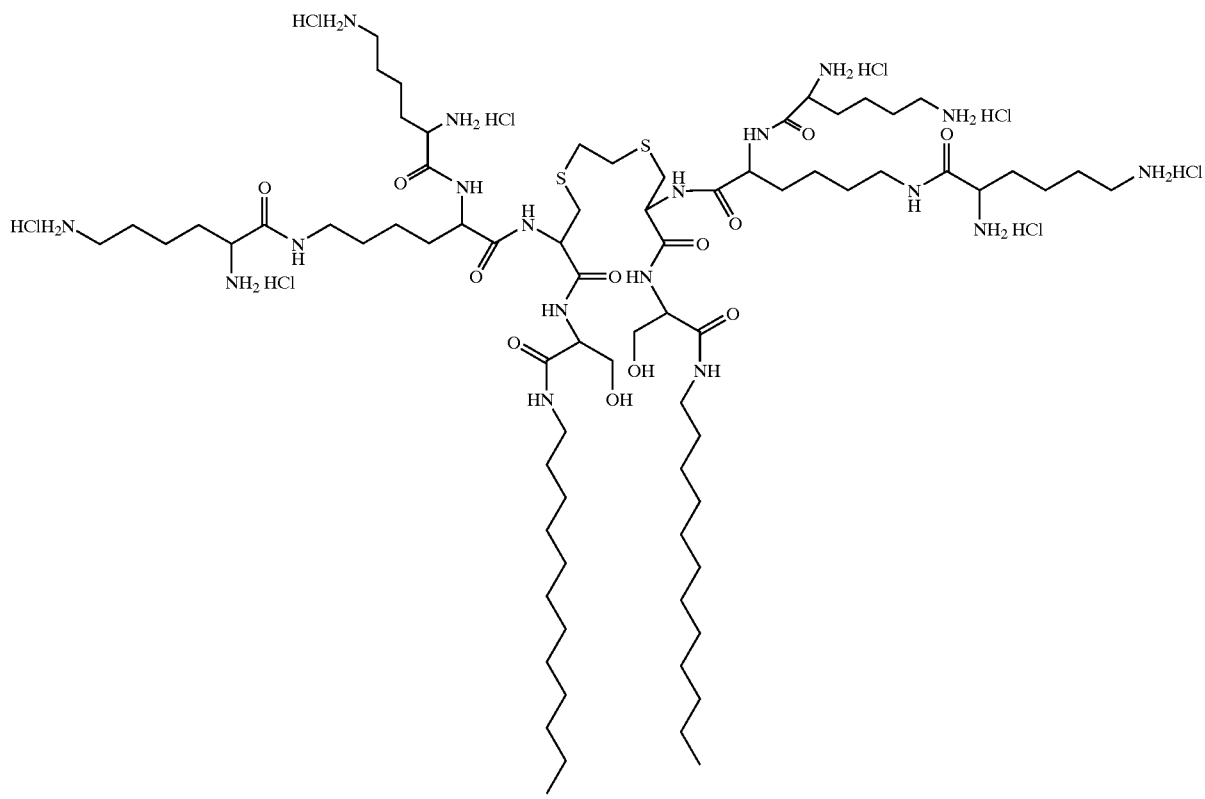

Example 16
Compounds 57, 58 and 59
Compounds 57, 58 and 59 are synthesised in a similar manner to the compounds described above. Compound 39, or an intermediate equivalent to compound 39 but having different saturated or unsaturated hydrocarbon chains, is combined with an ornithine compound using synthetic peptide chemistry well known to the skilled person.
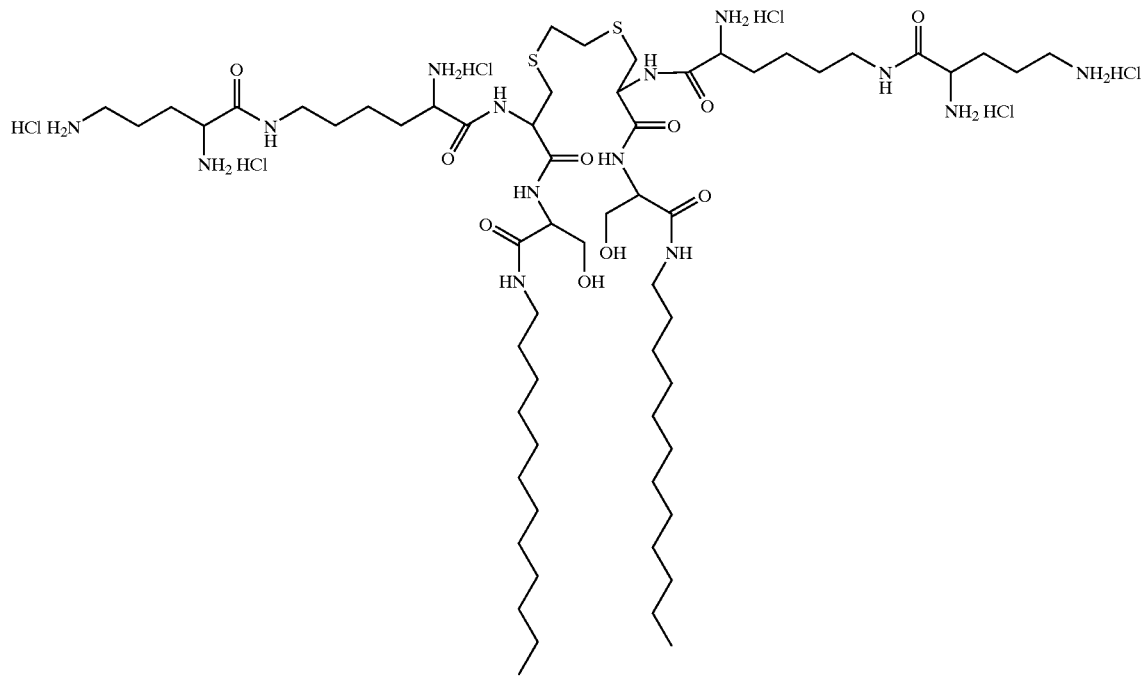
57
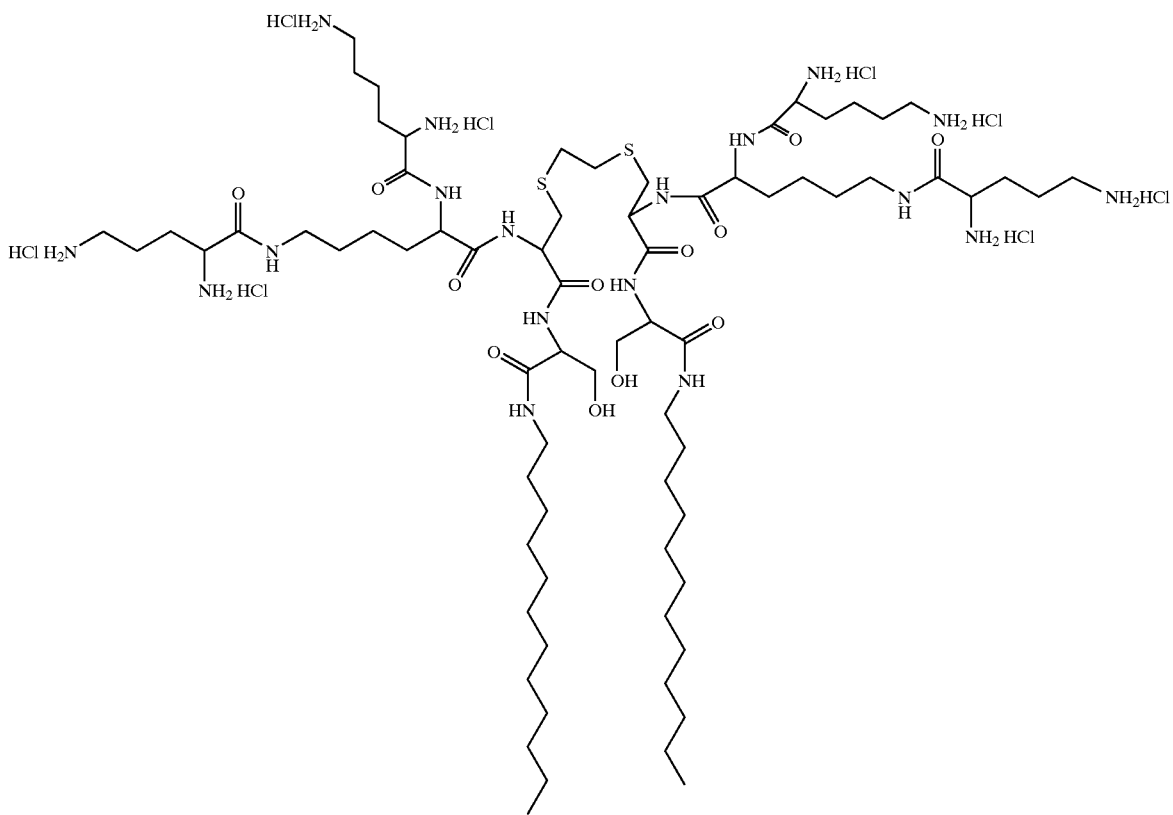
58

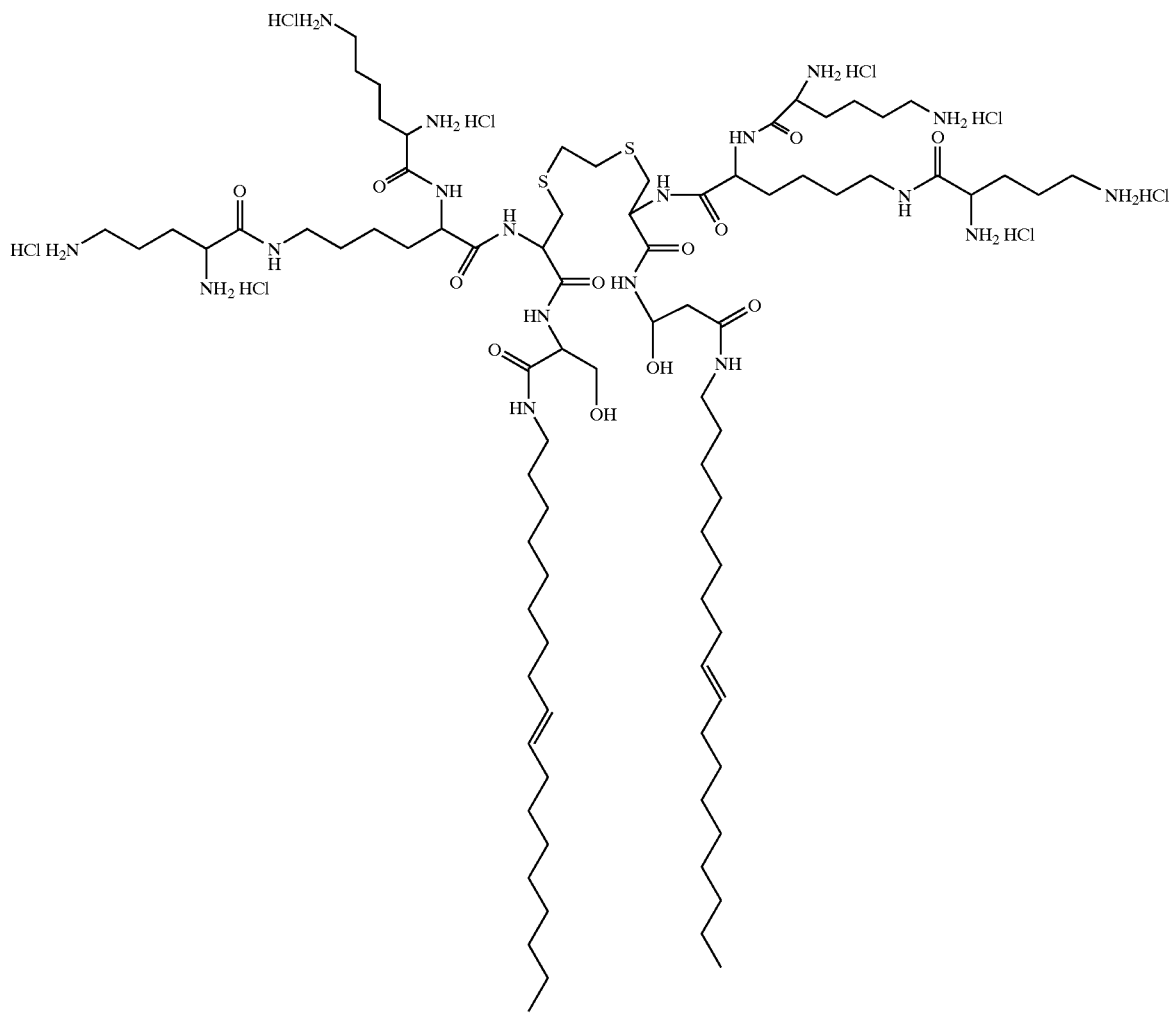

59

It will be appreciated by a person skilled in the art that in the formulae shown in the examples above, the hydrogen atoms have been omitted from the N, C and O atoms, where appropriate, for clarity.

Example 17

Transfection of Recombinant Plasmid Expressing Luciferase Into HEK293 Cells Using Peptide-based Gemini Compounds.

All tissue culture reagents were obtained from Life Technologies Inc. HEK 293 cells were seeded at $2-3 \times 10^5$ cells per well in Nunc six-well culture plates, 24 hours prior to transfection. The cells were seeded in 2 mls Dulbeccos Modified Eagle medium containing Earles salts and supplemented with 10% v/v foetal bovine serum (=complete medium). The cells were grown at 37° C. in 5% $CO_2$ in a humidified atmosphere. 6 ug DNA ("luciferase control plasmid" from Promega Corp.) were dissolved in 100 ul serum free medium (OPTI-MEM®). The peptide-based gemini compounds were made up at 1 mg/ml in tissue culture grade water and then diluted in OPTI-MEM® to the appropriate concentration to a final volume of 10 ul. The DNA and gemini solutions were mixed (to a total volume of 200 ul; final concentrations of 5, 25, 50, 100, 150, 200, 250 and 300 ug/ml) and left at room temperature for 15 minutes. The DNA/gemini mix was placed onto the cells in each well and left in contact for 18–20 hours. The cells were then washed twice with phophate buffered saline prior to 1 ml of fresh complete medium being added. Cells were incubated for a further 24 hours prior to lysis and luciferase activity assayed.

All luciferase activity assays were performed using the Canberra Packard (Berkshire, UK) Luclite kit according to the manufacturer's instructions with the exception that the cells in each well were resuspended in 1 ml lysis buffer and 10 ul aliquots mixed with 100 ul of the luciferase substrate. The reaction mix was left for a 15 minutes adaptation period in the dark before counting for 5 minutes in a Top Count scintillation counter. Luciferase activity is measured as counts per second (CPS) from the scintillation counter. Four independent counts were taken per well.

Control transfections were set up with no DNA, $CaPO_4$, an anionic gemini compound (1) and the commercially available lipofection reagents LipofectAmine™ and Lipotaxi™ at the manufacturers recommended concentrations (10, 25, 50, 75, 125 ug/ml and 175, 250, 325, 400 and 500 ug/ml respectively).

The results (FIG. 1) clearly show that the cationic peptide-based gemini compounds (54), (55) and (56) are very efficient agents for facilitating the transfection of the luciferase plasmid into HEK293 cells at concentrations above 150 ug/ml. In particular compound (54) peaks at 250 ug/ml with a mean count (of 4 independent counts) of over 70,000 cps. Compound (55) is most effective at 300 ug/ml with an average count of about 45,000 cps. Compound (56) is most effective at 200 ug/ml with an average count of about 50,000 cps. In contrast the 'no DNA' negative control gives a background count as do the anionic gemini (1) and the cationic geminis (50 and 52). The $CaPO_4$ transfection shows a very low count of about 2,000 cps. In comparison FIG. 2 shows the results for the Lipofectamine transfections which at peak efficiency gave only 12,500 cps (125 ug/ml) and Lipotaxi 2,500 cps (at 175 ug/ml and 325 ug/ml).

Example 18

Transfection of Recombinant Plasmid Expressing Luciferase Into CHO-K1 Cells Using Peptide-based Gemini Compounds.

CHO-K1 cells (ATCC: CRL-9618) were seeded into $T_{25}$-culture flasks (Corning-Costar Buckinghamshire, UK), at $7 \times 10^5$ cells per flask, 24 hours prior to transfection. The CHO-K1 cells were seeded in 5 ml MEM alpha medium with ribonucleosides and deoxyribonucleosides and supplemented with 1×L-glutamine and 10% v/v foetal bovine serum (complete medium). The cells were grown at 37° C. in 5% $CO_2$ in a humidified atmosphere.

For transfection, 5 ug DNA (luciferase control plasmid) was incubated with the gemini compounds in water (final volume 400 μl). The peptide-based gemini compounds were made up at 1 mg ml$^{-1}$ in tissue culture grade water and then diluted to the appropriate concentration to a total volume of 200 μl. Following a 30 minute room temperature incubation, 2.6 ml OPTI-MEM® medium was added and the solution placed on the cells. Following an overnight incubation at 37° C., the transfection solution was replaced with complete medium and the cells incubated at 37° C. 24 hours post transfection the cells were detached from the flask and seeded into 96-well plates at a density of $0.5 \times 10^5$ cells per well and incubated for a further 24 hours at 37° C. Luciferase reporter gene assays were performed according to the manufacturers instructions (Roche Diagnostics, Mannheim, Germany) approximately 48 hours post transfection. The plates were left for a 15 minutes adaption period in the dark before counting for 60 seconds in a TopCount NXT counter (Canberra Packard). An average of eight wells were counted per transfection.

Control transfections were set up with no DNA, an anionic gemini compound and the commercially available reagent LipofectAmine PLUS™.

The results, shown in FIG. 3, demonstrate that the cationic peptide-based compounds 54, 55, and 56 are very efficient agents for facilitating the transfection of the luciferase plasmid into CHO-K1 cells. Using the conditions described above, compound 54 peaks at 30 mM with a mean count in excess of $1.4 \times 10^5$ counts per second (cps). Compound 55 is most effective at 30 mM with an average count of about $2.4 \times 10^5$ cps. Compound 56 is most effective at 40 mM with an average count of about $1.9 \times 10^5$ cps. In contrast negative controls gave a negligable count.

Example 19

Transfection of Recombinant Plasmid Expressing Luciferase Into CHO-K1 Cells Using Peptide-based Gemini Compounds in Combination With Various Supplements.

The transfection ability of the gemini compounds could be further enhanced by the addition of a neutral carrier, for example, dioleyl phosphatidylethanolamine (DOPE) (Farhood, H., et al (1985) *Biochim. Biophys. Acta* 1235 289) or a complexing reagent, for example, PLUS compound (Life Technologies Inc.).

FIG. 4 shows, for example, a 9-fold increase of luciferase activity at a 2:1 ratio of compound 55 and DOPE. Transfection mediated by compound 55 with DOPE in a 2:1 ratio and the addition of 11.6 ul of PLUS compound lead to a mean count of $6.5 \times 10^5$ cps representing a 12-fold increase of luciferase activity in comparison to compound 55 alone. Incubation of the PLUS compound with the DNA and combination with compound 55 alone also lead to a 4-fold increase.

Example 20

Use of Peptide-based Gemini Compounds to Facilitate Adhesion of Cells in Culture to the Culture Flask.

Using normal growth medium and culture conditions (RPMI plus 10% foetal bovine serum; 37° C., 5% $CO_2$) but with the addition of 50–60 ug peptide-based gemini compound per well, it was observed that with the suspension cell line Jurkat, cells could attach to the bottom surface of the plastic culture vessel. In the absence of gemini compounds, the Jurkat cells grew in suspension.

Figure 1:
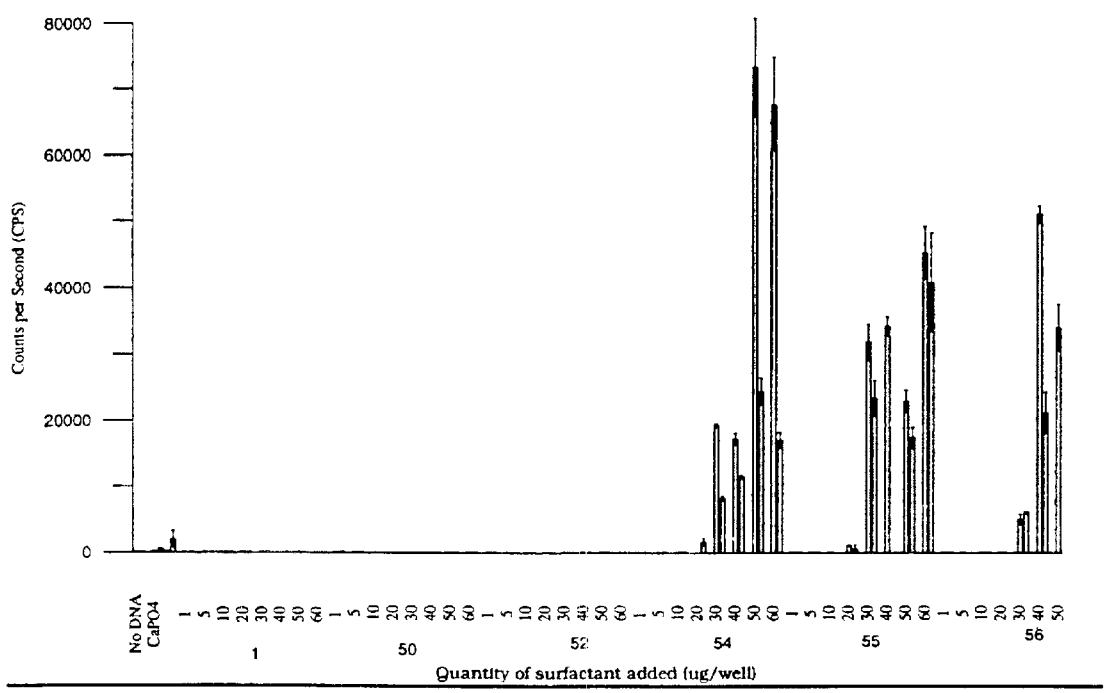
FIG. 1. Transfection of HEK 293 cells gemini compounds (1), (50), (52), (54), (55), (56). Bars represent the mean cps of four aliquots from duplicate wells.
Figure 2:
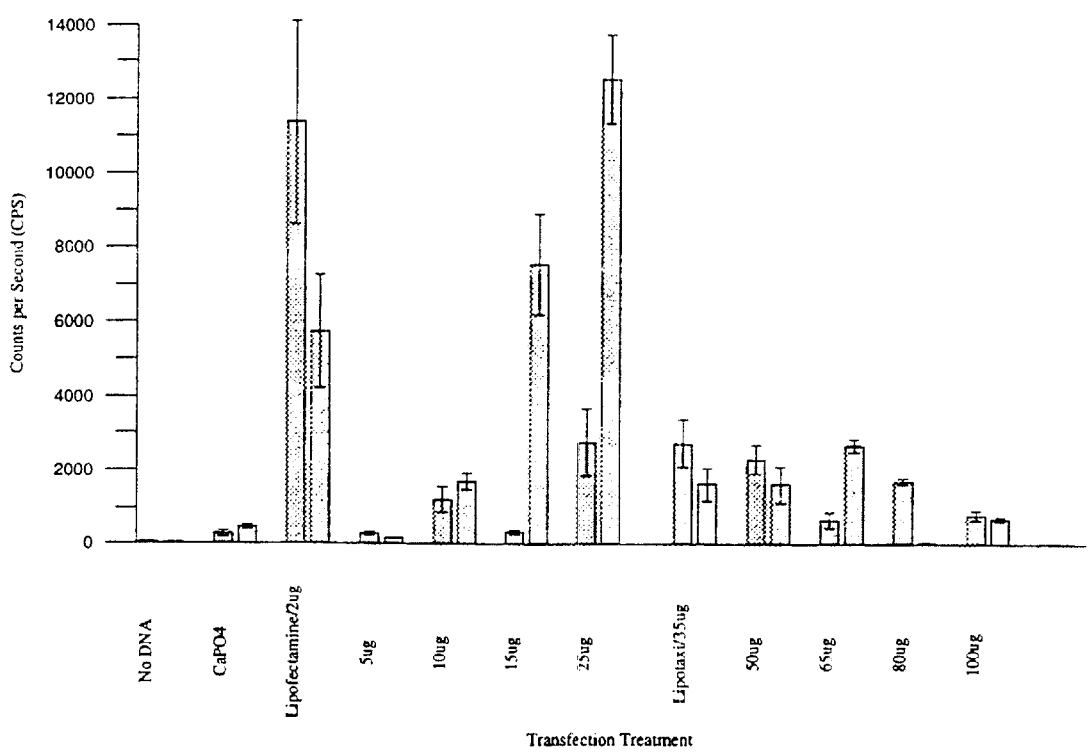
FIG. 2. Transfection of HEK 293 cells with Lipofectamine™ and Lipotaxi™ at manufacturers recommended concentrations. Bars represent the mean cps of four aliquots from duplicate wells.
Figure 3:
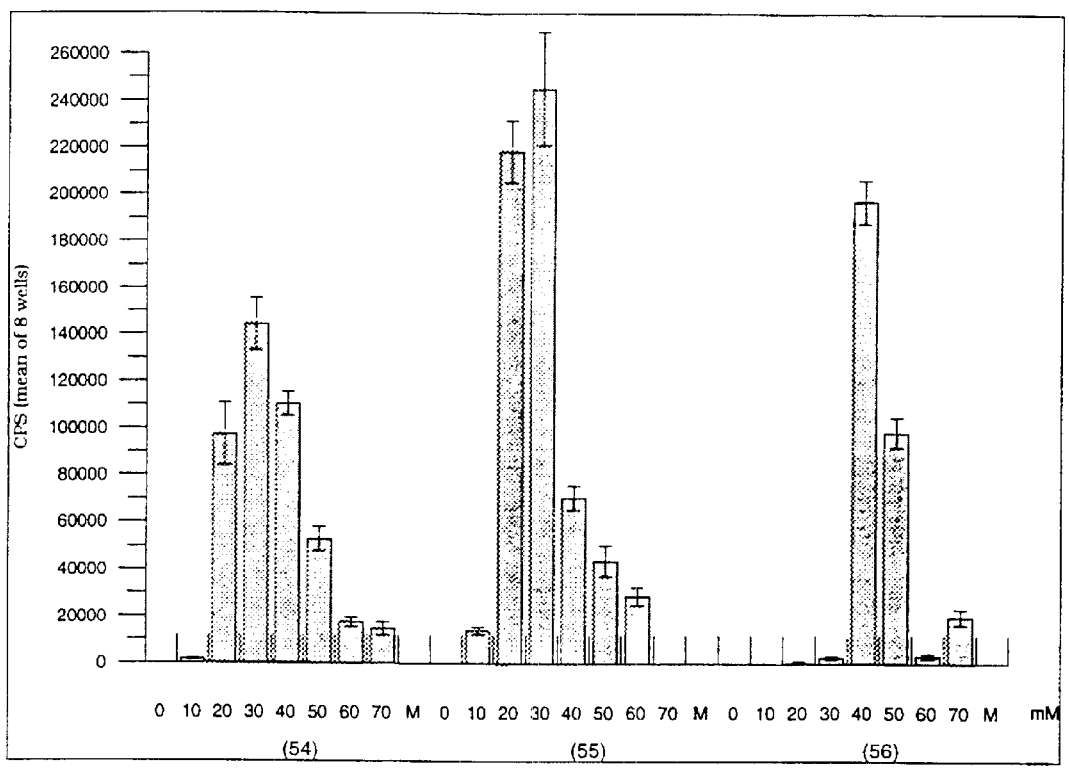
FIG. 3. Transfection of CHO-K1 cells with gemini compounds (54), (55), and (56). Bars represent the mean cps of 8 wells±the standard error of the mean.
Figure 4:
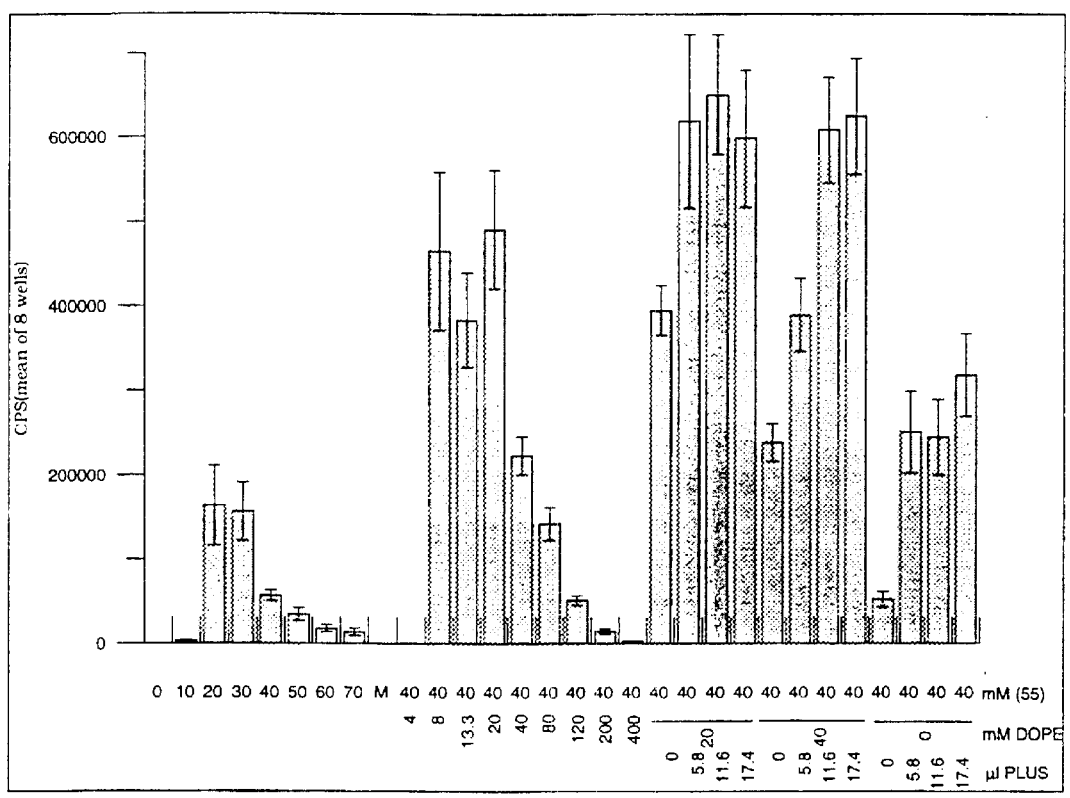
FIG. 4. Transfection of CHO-K1 cells with gemini compound 55 with the addition of DOPE alone and/or PLUS. Bars represent the mean cps of 8 wells±the standard error of the mean.

What is claimed is:

1. A peptide-based gemini compound according to the formula (I):

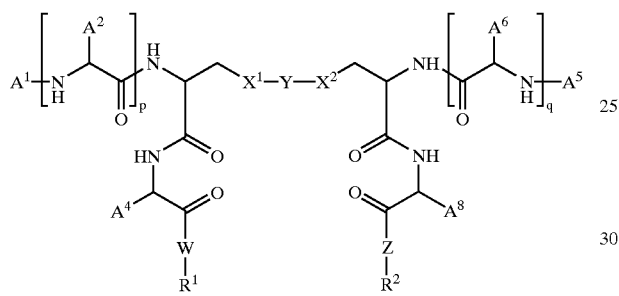

(I)

where:
- $A^1$ and $A^5$, which may be the same or different, are positively charged groups formed from one or more amino acids or amines joined together in a linear or branched manner;
- $A^2$ is the side chain of an amino acid;
- $A^6$ is the side chain of an amino acid;
- p and q, which may be the same or different, is 0 or 1;
- $X^1$ is O or S;
- $X^2$ is O or S;
- $A^4$ is $CH_2OH$ or $CH(CH_3)OH$;
- $A^8$ is $CH_2OH$ or $CH(CH_3)OH$;
- Y is a linker group, or when each of $X^1$ and $X^2$ is S, the group of variables $X^1$—Y—$X^2$ taken together represents a disulfide bond;
- $R^1$ and $R^2$ are $C_{(10-20)}$ saturated or unsaturated alkyl groups, and
- W and Z are NH, O, $CH_2$ or S; or a salt thereof.

2. A compound according to claim 1 wherein $A^1$ and $A^5$ are each a D- or L-amino acid selected from arginine, lysine, ornithine and histidine.

3. A compound according to claim 1 wherein $A^1$ and $A^5$ each have up to 7 amino acids linked in a linear or branched chain.

4. A compound according to claim 3 wherein $A^1$ and $A^5$ each have two or three lysines or ornithines or a combination of lysine, ornithine, arginine and histidine.

5. A compound according claim 1 wherein $A^2$ is the side chain of the amino acid serine, and $A^6$ is the side chain of the amino acid serine.

6. A compound according to claim 1, wherein Y is $(CH_2)_m$, where m is an integer from 1 to 6.

7. A compound according to claim 1 wherein each of $X^1$ and $X^2$ is S, and the group of variables $X^1$—Y—$X^2$ taken together represents a disulfide bond.

8. A compound according to claim 6 wherein m is 2.

9. A compound according to claim 1 wherein $R^1$ or $R^2$ is $C_{12}$ alkyl.

10. A compound according to claim 1 wherein W and Z are NH.

11. A compound according to claim 1 wherein the salt is a pharmaceutically acceptable salt.

12. A compound according to claim 1 wherein $A^1$ and $A^5$ are the same, $A^2$ and $A^6$ are the same, $A^4$ and $A^8$ are the same, $R^1$ and $R^2$ are the some, and W and Z are the same.

13. The compound of formula 39

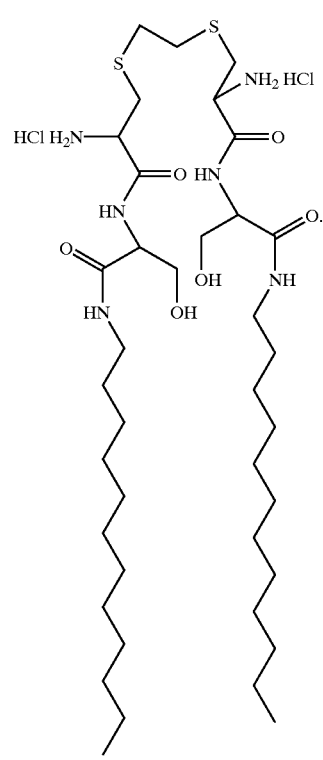

39

14. The compound of formula 55
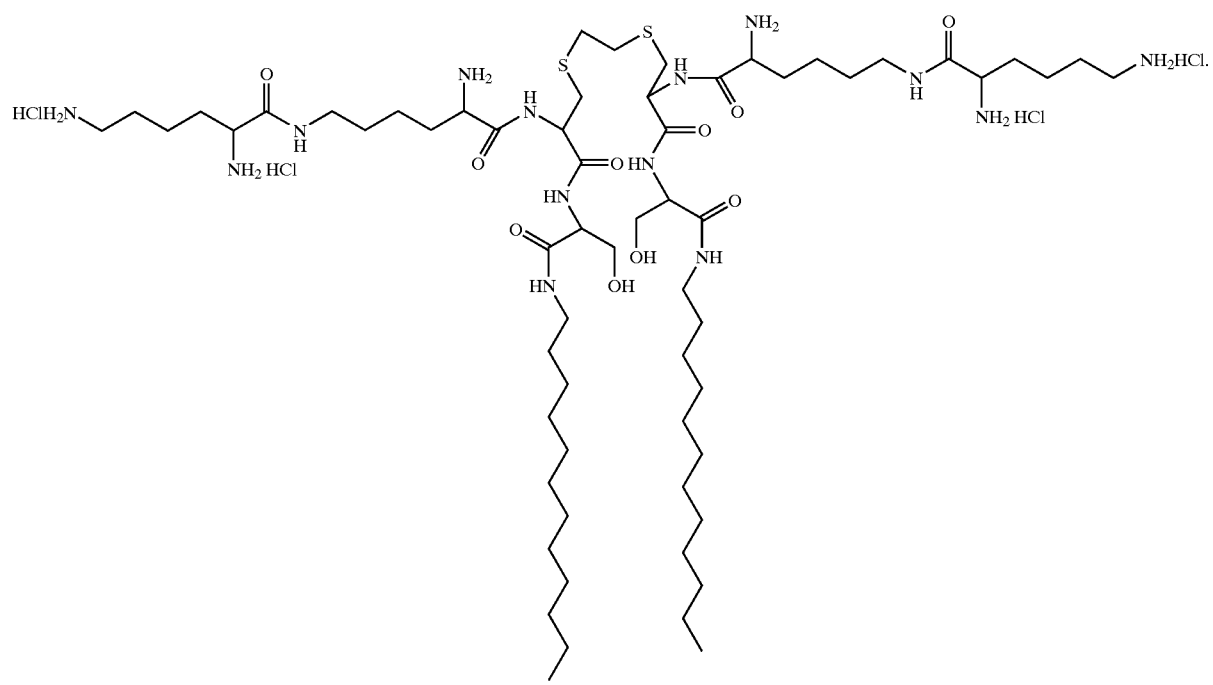
15. The compound of formula 56
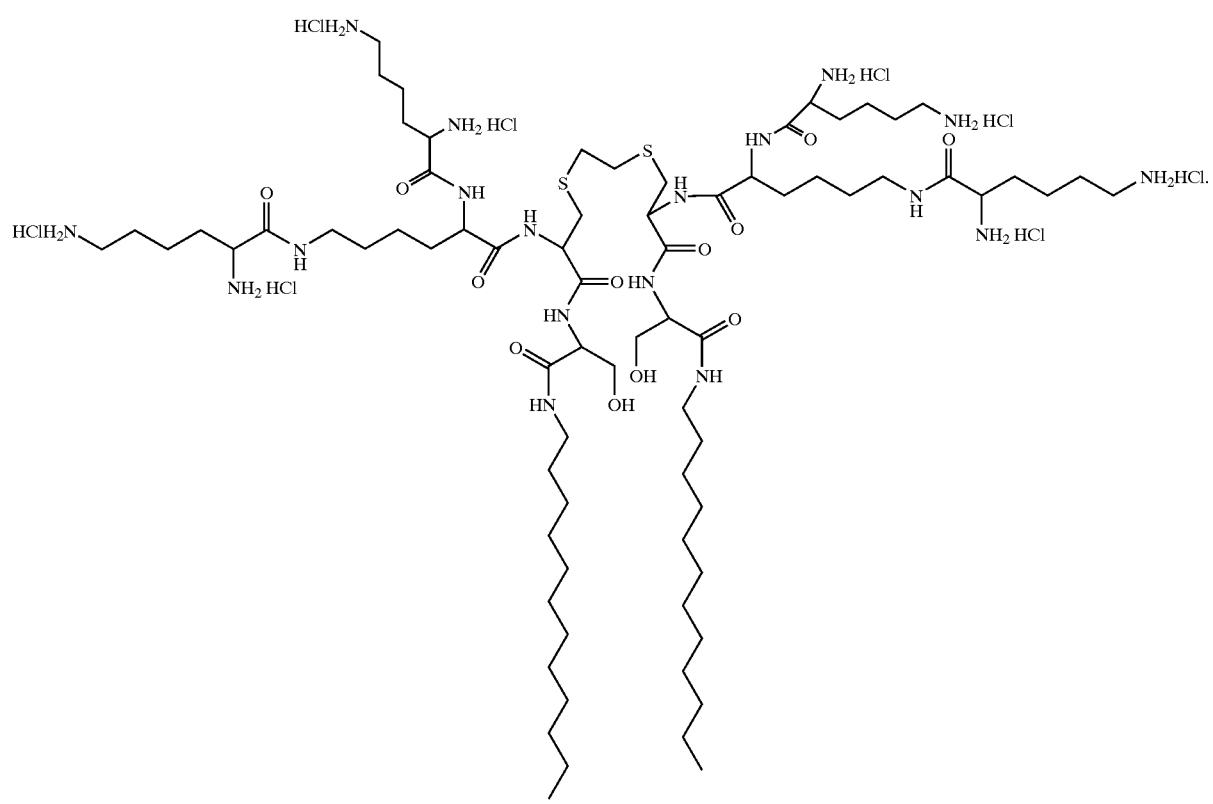

16. The compound of formula 57
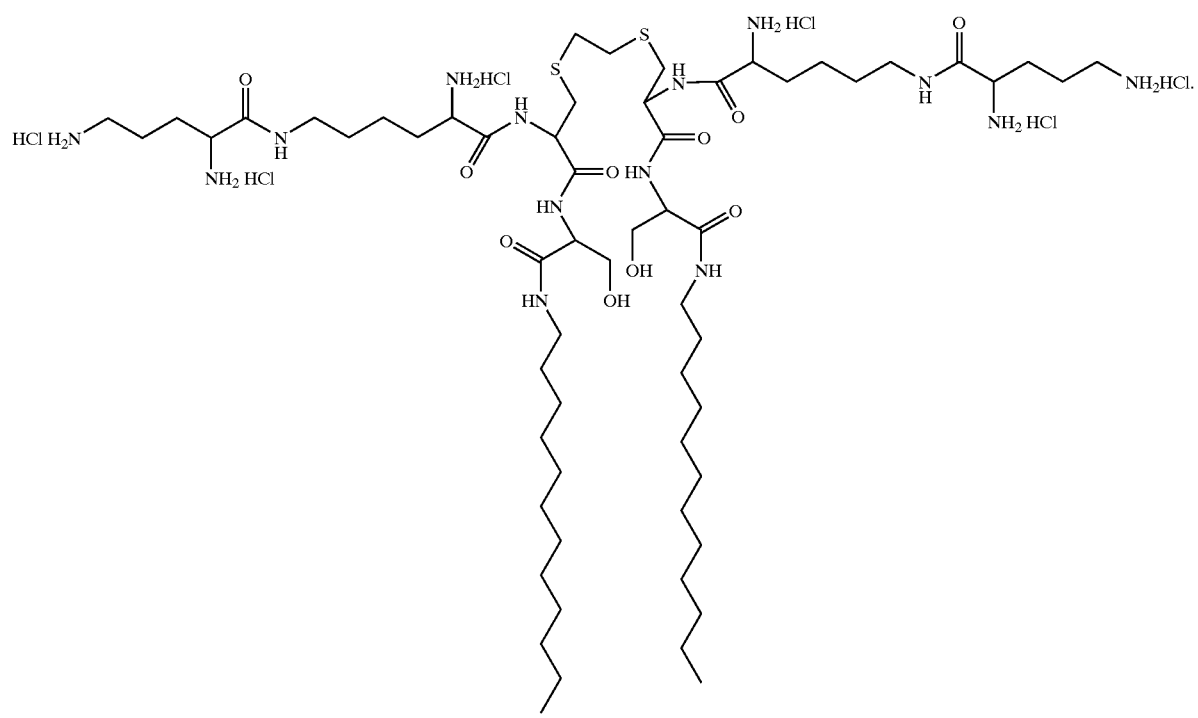
17. The compound of formula 58
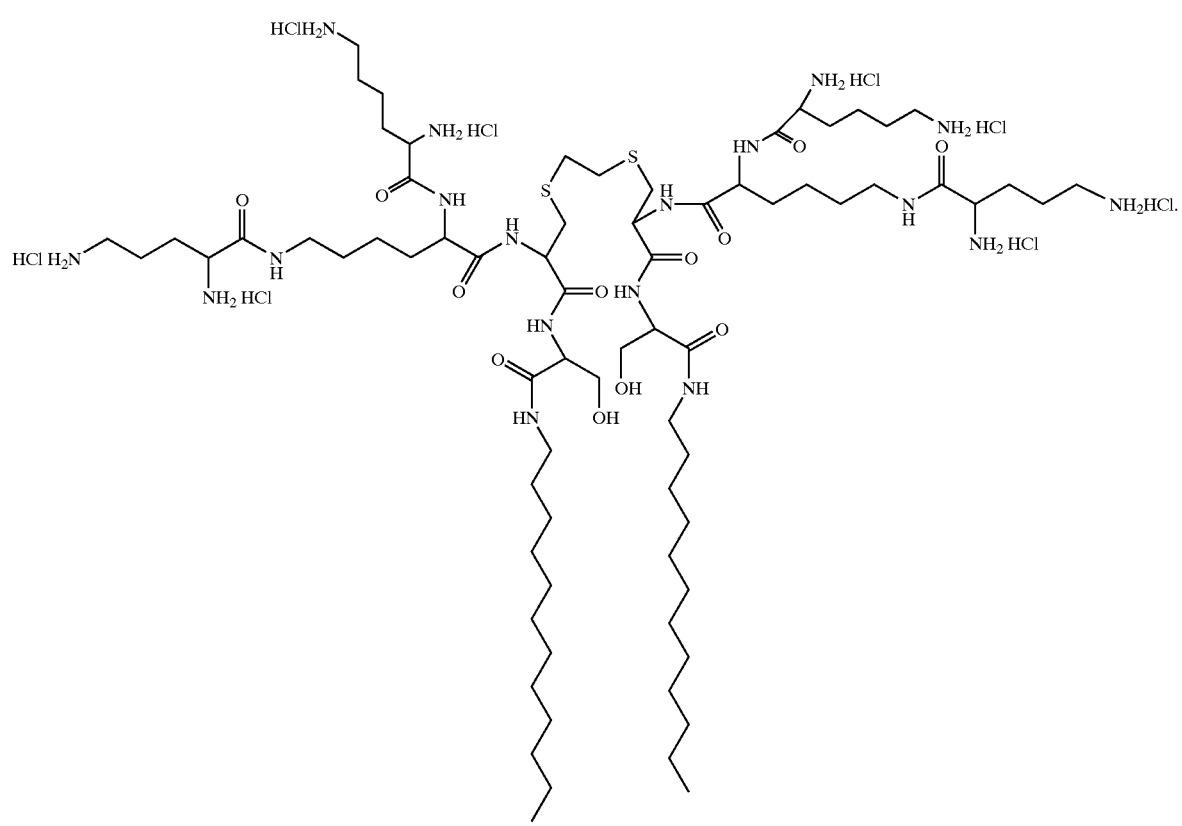

18. The compound of formula 59

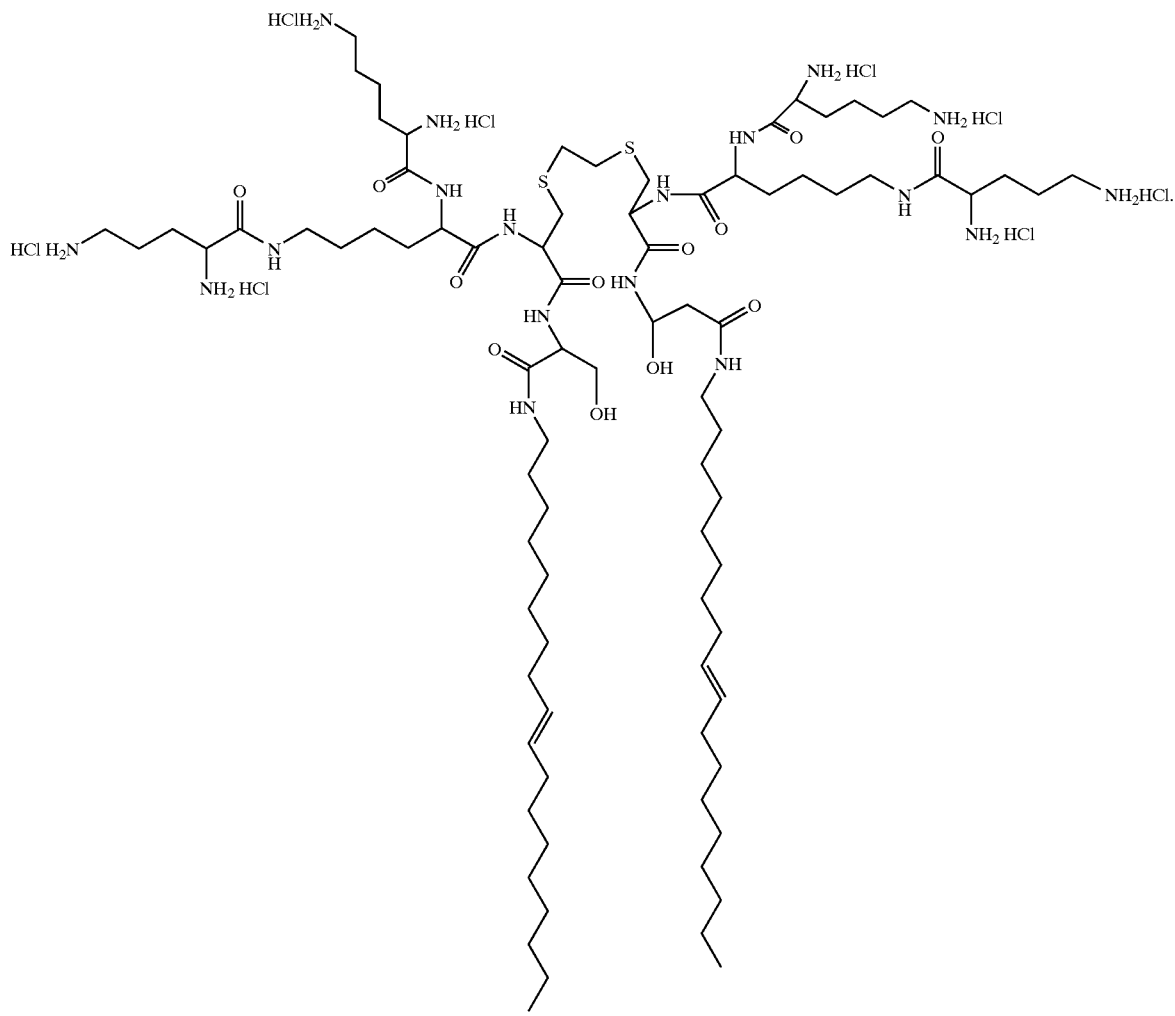

19. The compound according to claim 1 wherein p and q are both 1, $A^1$ is bonded to the NH group of the amino acid residue NHCH($A^2$)CO, and $A^5$ is bonded to the NH group of the amino acid residue NHCH($A^6$)CO.

20. The compound according to claim 1 wherein p and q are both 0, $A^1$ is bonded to the NH group of the amino acid residue bearing $X^1$ and $A^5$ is bonded to the NH group of the amino acid residue bearing $X^2$.

21. The compound according to claim 19 wherein each of $A^1$ and $A^5$ bears a terminal carbonyl group, and each said carbonyl group is bonded in amide linkage to each said NH group.

22. The compound according to claim 20 wherein each of $A^1$ and $A^5$ bears a terminal carbonyl group, and each said carbonyl group is bonded in amide linkage to each said NH group.

* * * * *